United States Patent [19]

Alexander

[11] Patent Number: 5,372,252
[45] Date of Patent: Dec. 13, 1994

[54] APPARATUS AND METHOD FOR DISPOSING MEDICAL INSTRUMENTS

[75] Inventor: K. Alexander, Royal Oak, Mich.

[73] Assignee: Life Force "2010", Southfield, Mich.

[21] Appl. No.: 116,616

[22] Filed: Sep. 7, 1993

[51] Int. Cl.⁵ .................... B65D 81/22; B65D 85/24
[52] U.S. Cl. ................................ 206/210; 206/366; 206/370; 422/25; 422/300
[58] Field of Search ............. 206/363, 365, 366, 370, 206/210, 205; 422/28, 25, 29, 26, 292, 300, 905

[56] References Cited

U.S. PATENT DOCUMENTS

| | | | |
|---|---|---|---|
| 3,876,067 | 4/1975 | Schwarz | 422/300 X |
| 4,232,784 | 11/1980 | Hesselgren | 422/300 X |
| 4,816,307 | 3/1989 | Honeycutt . | |
| 4,919,264 | 4/1990 | Shinall | 206/366 X |
| 4,936,449 | 6/1990 | Conard et al. . | |
| 5,038,929 | 8/1991 | Kubofcik | 206/210 |
| 5,230,426 | 7/1993 | Keefe et al. | 206/205 |
| 5,249,679 | 10/1993 | Dondlinger | 206/366 |
| 5,265,724 | 11/1993 | Dondlinger | 206/366 |
| 5,271,892 | 12/1993 | Hanson et al. | 422/25 |

*Primary Examiner*—Bryon P. Gehman

[57] ABSTRACT

A disposal assembly (10) includes a base (14) and four walls (20) extending perpendicularly out therefrom defining a hollow interior (22) partially filled with a plurality of layers. The bottom-most layer (38) is fabricated of styrofoam which, along with the tapered cylinders (28) and hydrostatic pressure, secures the medical instruments (12) therein. A layer of dry disinfectant (36) covers the styrofoam (38). A layer of sponge (34) directly covers the dry disinfectant (36). When fluid is injected into the dry disinfectant (36) to create a disinfectant solution, the sponge (34) absorbs the solution and distributes it across the entire cross section of the disposal assembly (10). A semi-viscous material (40) seals the disinfectant solution and the infected portions (26) of the medical instruments (12) in an anaerobic environment. The fluid is inserted into the dry disinfectant layer (36) by inserting a needle (50) through a hole (46) in the top plate (24) and through the semi-viscous (40) and sponge (34) layers. The needle (50) is stopped in the proper place, i.e., at the dry disinfectant layer (34), by a needle stop (54). A cap (56) is locked to the four walls (20) after the disposal assembly (10) is full.

10 Claims, 3 Drawing Sheets

APPARATUS AND METHOD FOR DISPOSING MEDICAL INSTRUMENTS

BACKGROUND ART

1. Technical Field

The invention relates to storing and disinfecting medical instruments prior to disposal. More particularly, the invention relates to a disposal assembly for storing and disinfecting medical instruments having a non-fluid disinfectant until the disposal assembly is used.

2. Description of Related Art

The advent of AIDS has brought new and safer ways of handling disposable medical instruments which contact bodily fluids. These disposable medical instruments ("medical instruments") include, but are not limited to, needles, syringes and the catheters.

One such disposal device is disclosed in U.S. Pat. No. 4,816,307, issued to Honeycutt on Mar. 28, 1989, wherein an apparatus is disclosed for storing the medical instruments and disposing of them. All of the medical instruments are inserted into a container wherein a liquid is poured over the medical instruments. After the liquid disinfects the medical instruments, the liquid hardens, via polymerization, immobilizing the medical instruments. The method and assembly are not ideal because the medical instruments are left unsecured and easily removable in the container until the liquid is poured into the container. This leaves a window of time for an accident to occur between the time an infected medical instrument is inserted into the container for eventual disinfection and disposal thereof and the time in which the container is completely filled. It is only after the container is filled to capacity that the hardening liquid is poured over the medical instruments.

U.S. Pat. No. 4,936,449, issued to Conard et al on Jun. 26, 1990 discloses a disposable device used for retaining and disposing of medical instruments. This system utilizes a layer of styrofoam to secure the medical instruments in the disposable container and further includes a disinfecting layer comprising of a wadding-type material soaked in a contaminant-neutralizing agent. This system is deficient is because the wadding soaked in the contaminant-neutralizing agent is not sealed from the outside atmosphere and will, therefore, have the tendency to dry up and become ineffective prior to filling the whole assembly with medical instruments.

Further, all of the assemblies disclosed in the prior art require the manufacturing, packaging, and shipping of liquids used as contaminant-neutralizing agents. Having this agent be in liquid form at the onset increases the costs of packaging and handling.

SUMMARY OF INVENTION AND ADVANTAGES

A disposal assembly is disclosed for disposing medical instruments after the use thereof. The disposal assembly comprises a base having a horizontal floor and at least one wall extending upwardly away from the horizontal floor. Receiving means is fixedly secured to the wall for receiving the medical instruments therein. Disinfecting means are disposed between the receiving means and the base for disinfecting the medical instruments. A styrofoam block is disposed above the base and secures the medical instruments in the disposal assembly. Sealing means seals the infected portions of the medical instruments and the disinfecting means from air located above the sealing means. The assembly is characterized by fluid inserting means for inserting fluid into the disposal assembly between the horizontal floor and the sealing means such that the sealing means continues to seal the infected portions and the disinfecting means after the fluid has been inserted below the sealing means.

The cost to manufacture the disposal assembly is greatly reduced because the disinfectant stored in the disposal assembly prior to usage is in a dry, solid form until the fluid is inserted through the fluid inserting means. This reduces the costs of manufacturing, packaging and shipping. Further, a second advantage associated with the invention is the ability of the disposal assembly to seal all air away from the infected portions of the medical instruments which reduces the life span of viruses such as HIV, AIDS, hepatitis B and C, and the like.

BRIEF DESCRIPTION OF THE DRAWINGS

Other advantages of the present invention will be readily appreciated as the same becomes better understood by reference to the following detailed description when considered in connection with the accompanying drawings wherein:

FIG. 4 is a side view of the preferred embodiment in a stacking relationship with another of the preferred embodiment of the invention.

DETAILED DESCRIPTION OF THE DRAWINGS

Figure 1:
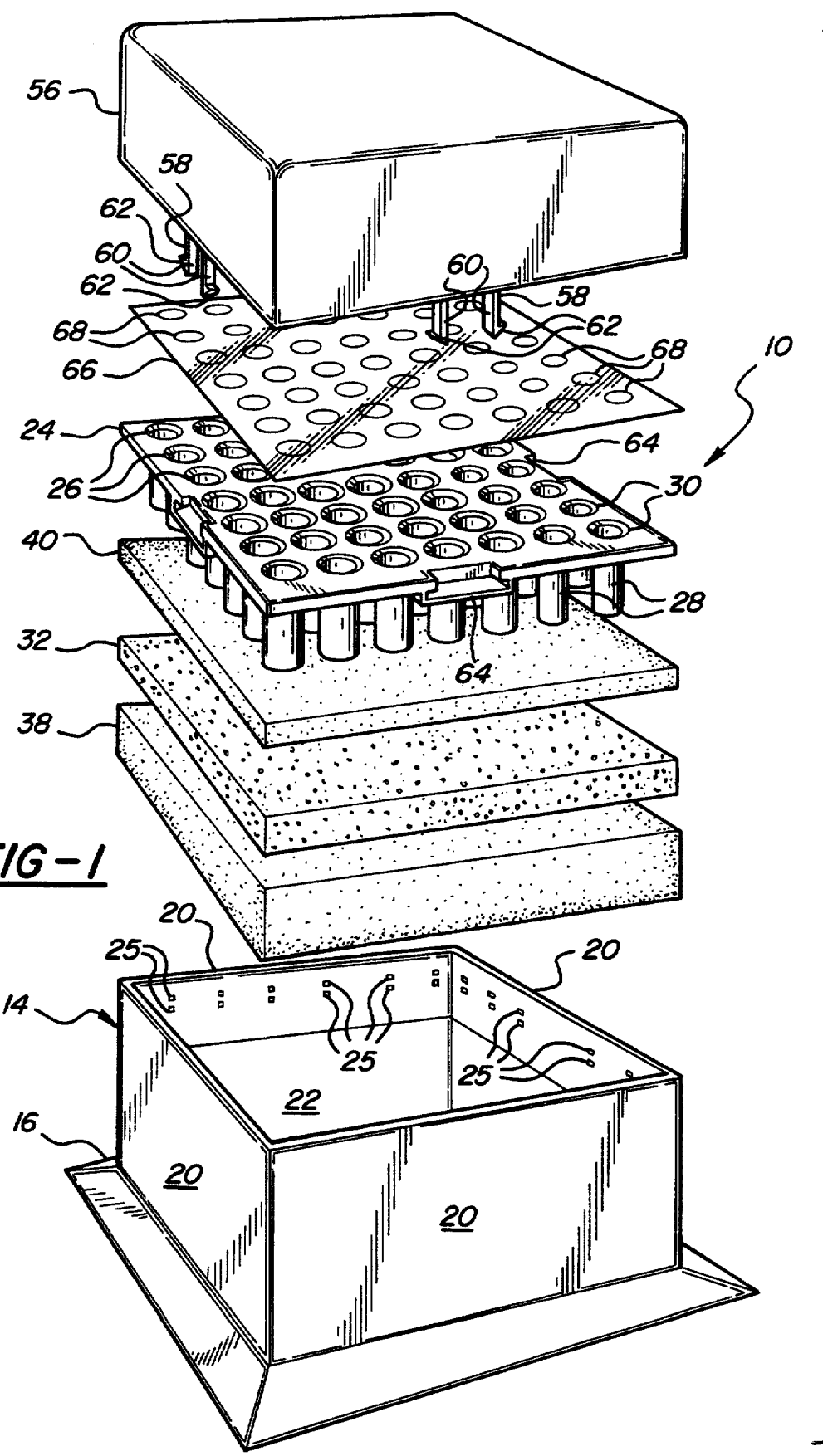
FIG. 1 is an exploded perspective view of the preferred embodiment of the invention.
Figure 2:
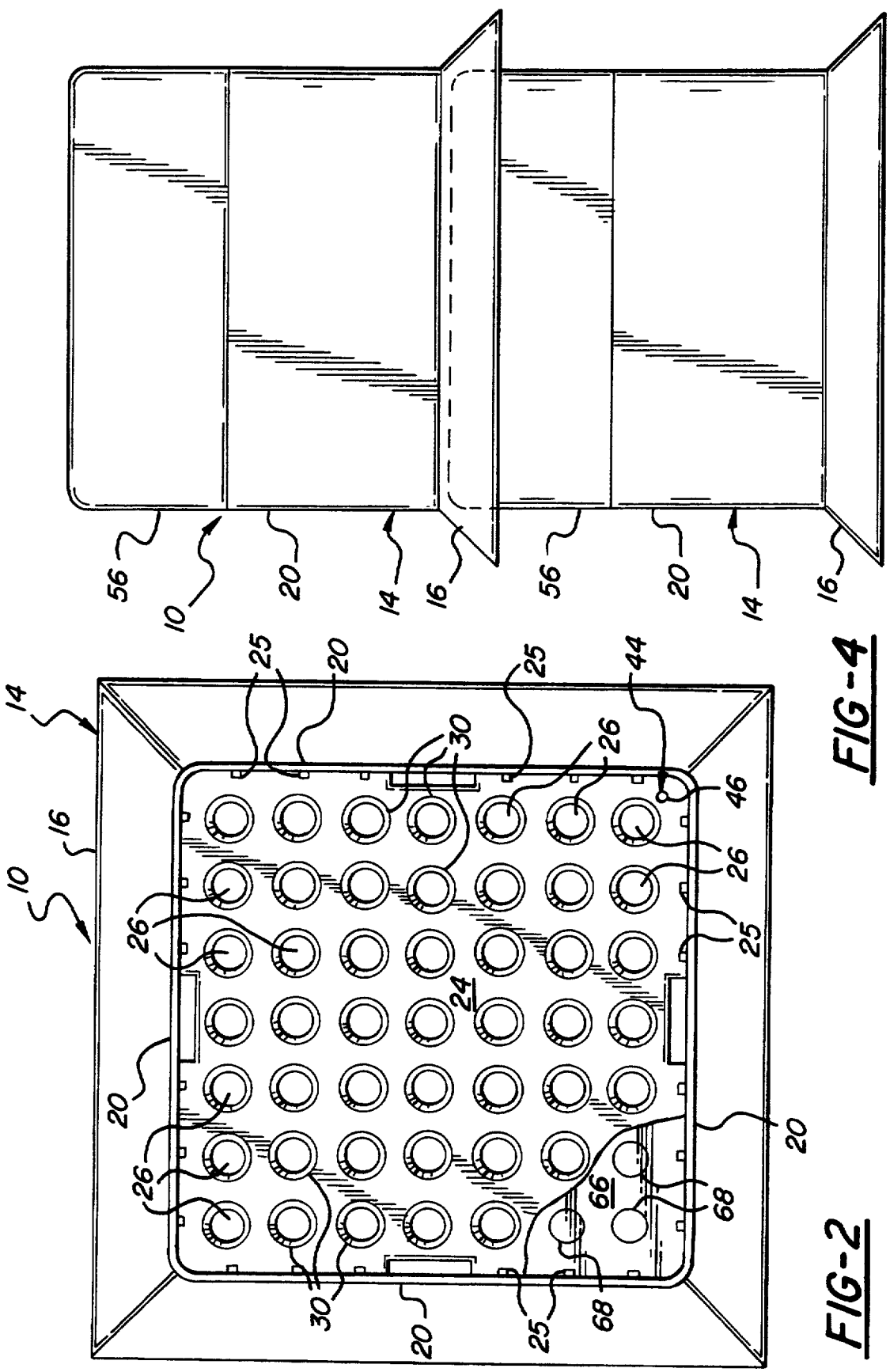
FIG. 2 is a top view partially cut away of the preferred embodiment of the invention.
Figure 3:
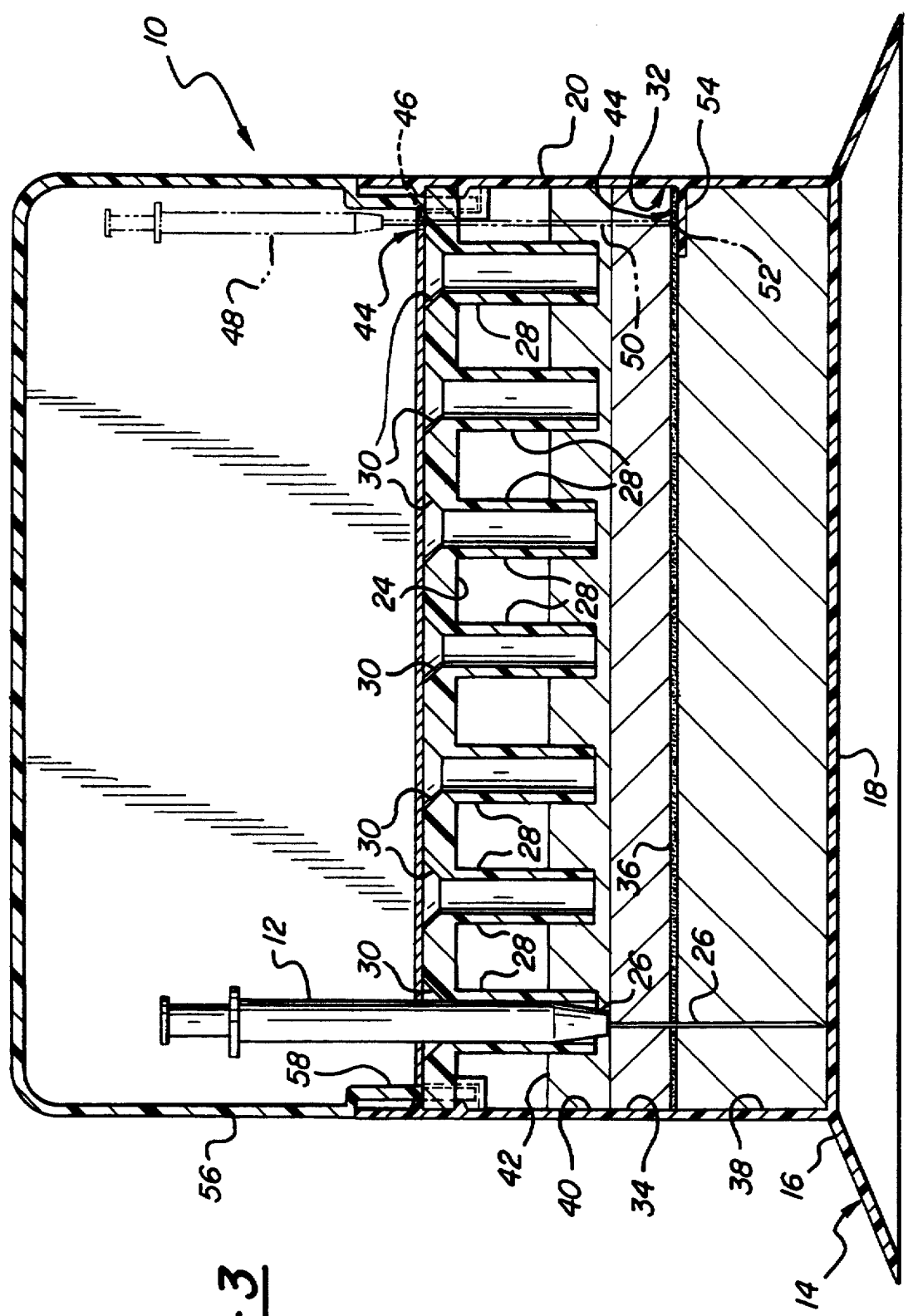
FIG. 3 is a cross-sectional side view of the preferred embodiment of the invention with an infected medical instrument inserted therein and a fluid inserting needle shown in phantom.

With reference to the drawings, the invention is a disposal assembly and is generally indicated at 10. The disposal assembly 10 is used for disposing medical instruments 12 after the medical instruments 12 have been used. The medical instruments may include any type of sharp instrument which has contacted bodily fluids of a patient. The preferred embodiment of the disposal assembly 10 is designed to receive such medical instruments as needles, syringes, and catheters. It is, however, conceivable that other instruments may be disposed of in this disposal assembly 10 with slight modifications to the holes 26 (discussed subsequently); such instruments being scalpels, scissors, and other such surgical instruments well known in medical fields.

A base, generally shown at 14, includes a broadened portion 16 which lowers the center of gravity of the disposal system 10 reducing the risks of tipping the disposal assembly 10 over. The broadening portion 16 also allows for the receipt of the top of a cap 56 of a second disposal assembly 10 for stacking engagement therebetween, as best shown in FIG. 4. The base 14 further includes a flat horizontal surface 18 which extends between the broadened portions 16 of the base 14. The base 14 further includes at least one wall 20 which extends upwardly away from the base 14. In the preferred embodiment, four walls 20 extend upwardly along the periphery of the horizontal floor or surface 18 of the base 14 wherein all of the walls 20 are perpendicular to each other and the horizontal floor 18. All of the four walls 20 are fixedly secured to each other and the horizontal floor 18 to define a hollow interior space 22.

Receiving means 24 is fixedly secured to the walls 20 via tabs 25 for receiving medical instruments 12 therein. The receiving means 24 is a plate having a plurality of holes 26 therethrough. Tapered tubes 28 extend down from the holes 26 perpendicular to the plate 24. A beveled edge 30 extends up and out away from the holes 26 to create a larger hole at the top of the plate 24. The beveled edge 30 aids in the guiding of a medical instrument 12 down into the tapered tube 28. In alternative terms, the beveled edge 30 guides the medical instrument 12 down through the tapered tube 28 reducing the requirements on the user to be accurate in placing the medical instrument 12 therein. The taper in the tubes 28 helps maintain the medical instruments 12 in the assembly 10.

Disinfecting means, generally shown at 32 is disposed between the plate 24 and the base 14 and disinfects the infected portions 26 of the medical instruments 12. The disinfecting means 32 includes a sponge layer 34 which absorbs fluid (discussed subsequently) which is inserted into the hollow interior space 22 prior to the insertion of any medical instruments 12 therein. The sponge layer 34 may be any type of material which is capable of absorbing fluid and holding the fluid for a time only determined by the ability of the fluid to evaporate. More specifically, the sponge layer 34 may be any material capable of absorbing and holding a fluid for an indefinite amount of time.

The disinfecting means 32 further includes a layer of disinfecting solute 36 which is mixed with the fluid which is inserted into the hollow interior space 22 to form a disinfecting solution wherein the fluid is the solvent of the solution. In the preferred embodiment, the disinfecting solute 36 is a layer of dry bleach which is easily dissolved into the fluid, typically water, creating a bleach solution which can effectively kill viruses, especially with the aid of an anaerobic environment (discussed subsequently). Enough dry bleach is present to create a two percent (2%) bleach solution, well in excess of what is necessary to kill any virus present. A block of styrofoam 38 is located directly below the layer of bleach 36 and helps secure the medical instruments inside the disposal assembly 10. The styrofoam 38 is the desired material because it will sufficiently secure a needle or catheter therein and, yet, it will not absorb any of the bleach solution which is directly above the block of styrofoam 38.

The disposal assembly 10 further includes sealing means 40 for sealing the infected portions 26 of the medical instruments 12 and the disinfecting means 32 from air located above the sealing means 40. The sealing means 40 enables the infected portions 26 of the medical instruments 12 to be stored in an anaerobic environment decreasing the life span of any viruses which may be found on the infected portions 26. The sealing means 40 includes a semi-viscous silicone based material which is capable of surrounding the medical instruments 12 to prevent the air from contacting the infected portions 26 of the medical instruments 12. Obviously, the sealing means 40 does not have to be silicone based and can be any viscous or semi-viscous gel based material which is impervious to the constant contact of a bleach solution thereto. A mylar film 42 extends above the semi-viscous silicone based material 40 to prevent the semi-viscous material 40 from shifting to one side destroying the seal or from enveloping air pockets both of which may increase the life span of the viruses found on the infected portions 26 of the medical instruments 12. The tapered tubes 28 act as baffles to help prevent the shifting of the semi-viscous fluid 40. Once the mylar fiber 42 has been pierced and a medical instrument 12 has been fully inserted, the semi-viscous fluid 40 slowly rises up around a portion of the medical instrument 12 further sealing the infected portions 26 of the medical instruments 12. The mylar film 42 and the semi-viscous fluid 40 combined to effectively create individual environments for each medical instrument 12.

The disposal assembly 10 is characterized by fluid inserting means, generally shown at 44, for inserting fluid into the disposal assembly 10 between the base 12 and the sealing means 40 such that the sealing means 40 continues to seal the infected portions 26 and the disinfecting means 32 after the fluid has been inserted below the sealing means 40. The fluid inserting means 44 includes a hole 46 in the receiving means 24 allowing a fluid injecting apparatus 48, shown in phantom, to pass therethrough. The fluid injecting apparatus 48 includes a needle 50 long enough to extend down beyond the semi-viscous material 40 and through the sponge layer 34 so that the tip 52 of the needle 50 abuts the layer of disinfecting solute or bleach 36. The fluid injecting apparatus or syringe 48 then is able to inject fluid, typically water, into the layer of disinfecting solute or bleach 36. Once the fluid is injected therein, the syringe 48 and needle 50 can be removed with the seal, provided by the semi-viscous silicone-based material 40, remains in tact by flowing into the area which has just been evacuated by the needle 50.

Therefore, the fluid injecting apparatus 44 allows for a continued anaerobic environment for the infected portions 26 of the medical instruments 12 in addition to a sealed environment 40 for the disinfecting means 32 which prevents the solvent, i.e., water, inserted by the fluid injecting apparatus 48 to evaporate rendering the disposal assembly 10 inoperative or partially ineffective.

Positioning means 54 positions the needle 50 adjacent the disinfecting means 32 such that the fluid injected by the needle 50 activates the disinfecting means 32. The positioning means 54 includes a stop 54 for stopping the needle 50 from passing thereby. If the needle 50 were to pass the layer of disinfecting solute 36, the fluid would be inserted into the block of styrofoam 38 rendering the disposal assembly 10 ineffective. The stop 54 is located directly between the block of styrofoam 38 and the layer of disinfecting solute or bleach 36. The stop 54 is a rectangular piece of hard material, typically plastic, extending out from the wall 20 perpendicular thereto in an area large enough to prevent the needle 50 from passing thereby given the needle is being inserted into the receiving means 24 through the hole 46.

A collapsible cap 56 is used to cover the medical instruments 12 and the disposal assembly 10 once the disposal assembly is filled, i.e., when all of the holes 26 have received medical instruments 12 therein. The collapsible cap 56 securely caps the disposal assembly 10 and prevents the access of the medical instruments 12 in the disposal assembly 10. Locking means 58 locks the capping means 56 to the wall 20. The locking means 58 includes parallelly extending arms 60 with hooks 62 at the distal ends thereof which are received by insertion portions 64 located in the top plate 24. Once the cap 56 is inserted over the disposal assembly 10 such that the hooks 62 engage the ends of the recesses 64, the only access available to the contents is by breaking the cap 56 off the disposal assembly 10. This feature adds considerable security to the invention when the disposal assembly 10 is being transported to a more permanent disposal facility.

A sheet of plastic 66 extends over the receiving means 24 to aid in further sealing the disposal assembly 10 from the outside air. The sheet of plastic 66 includes printed circles 68 thereon which help the user locate the holes therebelow when trying to insert a medical instrument 12 therein.

In operation, the collapsed cap 56 is removed from the disposal assembly 10 wherein the fluid injecting apparatus 48 is inserted into the fluid injecting port or hole 46. The needle 50 is forced down through the semi-viscous seal 40 and through the dry disinfectant 36. The needle 50 is then abutted up against the needle stop 54 and the fluid is injected into the dry disinfectant 36 wherein the fluid is distributed throughout the cross section of the disposal assembly 10. Once the dry disinfectant has been activated, i.e., once the dry disinfectant 36 has become a solute in a solution, the medical instruments 12 are inserted into the disposal assembly 10 to disinfect and store the medical instruments 12 therein. Once the disposal assembly 10 is full, the collapsible cap 56 is expanded and locked in place.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

I claim:

1. A disposal assembly (10) for disposing medical instruments (12) after the use thereof, said disposal assembly (10) comprising:

a base (14) having a horizontal floor (18) and a wall (20) extending upwardly away from said horizontal floor (18);

a receiving plate (24) fixedly secured to said wall (20) and adapted to receive medical instruments (12) having infected portions (26) therein;

a disinfecting means (32) disposed between said receiving plate (24) and said base (14) for disinfecting infected portions (26) of medical instruments (12);

a styrofoam block (38) disposed above said base (14) for securing medical instruments (12) in said disposal assembly (10);

a seal (40) to seal infected portions (26) of medical instruments (12) and said disinfecting means (32) from air located above said seal (40);

fluid inserting means (44) adapted to receive a fluid inserting apparatus (48) for inserting fluid into said disposal assembly (10) between said horizontal floor (18) and said seal (40) such that said seal (40) continues to seal the infected portions (26) and said disinfecting means (32) after the fluid has been inserted below the seal; and a stop (54) adapted to position a said fluid injecting apparatus (48) adjacent said disinfecting means (32) such that the fluid injected by the fluid injecting apparatus (48) activates said disinfecting means (32).

2. An assembly (10) as set forth in claim 1 further characterized by said fluid inserting means (44) including a hole (46) in said receiving plate (24) disposed above said stop (54) allowing a fluid injecting apparatus (48) to pass therethrough.

3. An assembly (10) as set forth in claim 2 further characterized by said seal (40) including a semi-viscous silicone-based material (40), said semi-viscous silicone-based material (40) preventing air from contacting the infected portion (26) of a received medical instrument (12).

4. An assembly (10) as set forth in claim 3 further characterized by said disinfecting portion (32) further including a layer of dry disinfectant (36) wherein said layer of dry disinfectant (36) mixes with the fluid such that the layer of dry disinfectant (36) becomes a solute and the fluid becomes a solvent.

5. An assembly (10) as set forth in claim 4 further characterized by said disinfecting means (32) further including a layer of sponge material (34) to absorb and evenly distribute the solution through all of said disinfecting means (32).

6. An assembly (10) as set forth in claim 5 further characterized by locking means (58) for locking a cap (56) to said wall (20).

7. An assembly (10) as set forth in claim 6 further characterized by said styrofoam block (38) located below said layer of dry disinfectant (36).

8. An assembly (10) as set forth in claim 7 further characterized by a sheet of plastic (66) extending over all of said receiving plate (24).

9. A method for transforming a disposal assembly (10) having a dry inactive disinfectant (36) into a disposal assembly (10) having a wet active disinfectant, the disposal assembly (10) including a layer of sponge (34) and a semi-viscous seal (40) sealing the disinfectant (36) and the layer of sponge (34) from the air outside the disposal assembly (10), a fluid injecting port (44) and a needle stop (54), the method comprising the steps of:

inserting a needle (50) into a fluid injecting port (46) in a disposal assembly (10);

forcing the needle (50) down through the semi-viscous seal (40) and through a dry disinfectant (36);

abutting the needle (50) up against a needle stop (54);

injecting a fluid into the dry disinfectant (36); and distributing the fluid throughout the disinfectant (36) and the layer of sponge (34).

10. A method set forth in claim 9 further characterized by inserting medical instruments (12) into the disposal assembly (10) after the fluid has been injected into the dry disinfectant (36).

* * * * *